United States Patent
Gloaguen et al.

(10) Patent No.: US 6,660,467 B1
(45) Date of Patent: Dec. 9, 2003

(54) VARIANT OF CILIARY NEUROTROPHIC FACTOR AND DNA ENCODING THE VARIANT

(75) Inventors: Isabelle Gloaguen, Scoppito l'Aquila (IT); Annalise Di Marco, Rome (IT); Anna De Martis, Rome (IT); Ralph Laufer, Rome (IT); Isabella Saggio, Rome (IT)

(73) Assignee: Instituto di Ricerche di Biologia Molecolare P. Angeletti S.p.A., Pomezia (IT)

( * ) Notice: Subject to any disclaimer, the term of this patent is extended or adjusted under 35 U.S.C. 154(b) by 0 days.

(21) Appl. No.: 09/381,393

(22) PCT Filed: Mar. 20, 1998

(86) PCT No.: PCT/IT98/00064
§ 371 (c)(1),
(2), (4) Date: Sep. 20, 1999

(87) PCT Pub. No.: WO98/41625
PCT Pub. Date: Sep. 24, 1998

(30) Foreign Application Priority Data

Mar. 20, 1997 (IT) .......................... RM97A0156

(51) Int. Cl.[7] .................. C12N 5/00; C12N 15/00; C07K 14/00; C07H 21/04

(52) U.S. Cl. .................... 435/4; 435/252.3; 435/320.1; 435/325; 435/375; 530/300; 530/399; 536/23.1; 536/23.5

(58) Field of Search .................. 424/85.1, 184.1, 424/198.1; 435/69.1, 70.1, 252.3, 320.1, 325, 375, 377, 4, 7.1, 410, 254.1, 255.1; 514/2, 12; 530/300, 350, 399; 536/23.1, 23.5

(56) References Cited

FOREIGN PATENT DOCUMENTS

| EP | 0 247 860 | 12/1987 |
| WO | WO 91/03259 | 3/1991 |
| WO | WO 93/10233 | 5/1993 |
| WO | WO 98/01149 | 1/1998 |
| WO | WO 98/22128 | 5/1998 |

OTHER PUBLICATIONS

Wells. J.A. Additivity of mutational effects in proteins. Biochemistry 29 (37): 8509–8517, 1990.*

Ngo et al. Computational complexity, protein structure prediction, and the Levinthal paradox. The Protein Folding Problem and Tertiary Structure Prediction, pp. 491–495, 1994.*

(List continued on next page.)

*Primary Examiner*—Elizabeth Kemmerer
*Assistant Examiner*—Bridget E. Bunner
(74) *Attorney, Agent, or Firm*—Sheldon O. Heber; Jack L. Tribble

(57) ABSTRACT

The subject of the present invention are variants of ciliary neurotrophic factor with enhanced receptor selectivity (CNTFR), useful for the treatment of diseases and disorders including motor neuron diseases and muscle degenerative diseases. Another subject of the invention is to provide a method for identifying the above mentioned CNTF variants. The hCNTF variants with the amino acid substitutions in accordance with the present invention, have a reduced ability, as compared to the human CNTF, to elicit biological effects through soluble CNTFR, without affecting its ability to activate membrane-bound neuronal CNTF receptors, thereby improving its therapeutic properties. FIG. 1 shows the reduced CNTFR binding affinity of a CNTF variant according to the invention (IA-CNTF; SEQ ID NO: 2). It is evident that the binding affinity of this variant to the CNTFR is reduced as compared to the wild-type human CNTF molecule.

10 Claims, 3 Drawing Sheets

OTHER PUBLICATIONS

Figure 1:
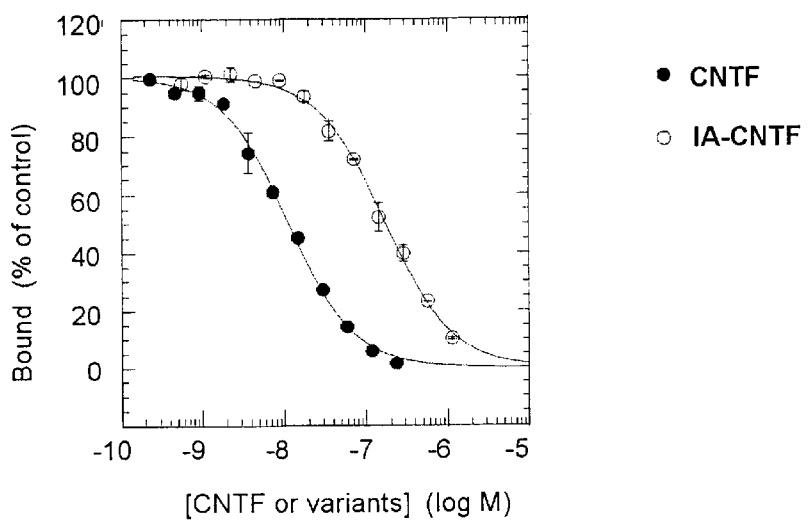

Di Marco et al. Identification of ciliary neurotrophic factor (CNTF) residues essential for leukemia inhibitory factor receptor binding and generation of CNTF receptor antagonists. Proc Natl Acad Sci USA 93(17): 9247–9252, 1996.*

Thier et al. Site–directed mutagenesis of human CNTF: functional analysis of recombinant variants. J Neurosci Res 40(6): 826–835, 1995.*

Di Marco, Annalise et al., "Agonistic and antagonistic variants of ciliary neurotrophic factor (CNTF) reveal functional differences between membrane–bound and soluble CNTF α–receptor.", Jour. Biol. Chem., vol. 272, No. 37, pp. 2306923075 (1997).

Saggio, Isabella et al., "CNTF variants with increased biological potency and receptor selectivity define a functional site of receptor interaction.", The EMBO Journal, vol. 14, No. 13, pp. 3045–3054 (1995).

* cited by examiner

SEQUENCE LISTING

```
<160> NUMBER OF SEQ ID NOS: 8

<210> SEQ ID NO 1
<211> LENGTH: 200
<212> TYPE: PRT
<213> ORGANISM: Homo sapiens

<400> SEQUENCE: 1

Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

Asn Leu Asp Ser Ala Asp Gly Met Pro Val Ala Ser Thr Asp Gln Trp
    50                  55                  60
```

```
Ser Glu Leu Thr Glu Ala Glu Arg Leu Gln Glu Asn Leu Gln Ala Tyr
 65                  70                  75                  80

Arg Thr Phe His Val Leu Leu Ala Arg Leu Leu Glu Asp Gln Gln Val
                 85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200

<210> SEQ ID NO 2
<211> LENGTH: 200
<212> TYPE: PRT
<213> ORGANISM: Homo sapiens

<400> SEQUENCE: 2

Met Ala Phe Thr Glu His Ser Pro Leu Thr Pro His Arg Arg Asp Leu
  1               5                  10                  15

Cys Ser Arg Ser Ile Trp Leu Ala Arg Lys Ile Arg Ser Asp Leu Thr
                 20                  25                  30

Ala Leu Thr Glu Ser Tyr Val Lys His Gln Gly Leu Asn Lys Asn Ile
             35                  40                  45

Asn Leu Asp Ser Ala Asp Gly Met Pro Val Ala Ser Thr Asp Gln Trp
 50                  55                  60

Ser Glu Leu Thr Glu Ala Glu Arg Leu Gln Glu Asn Leu Gln Ala Tyr
 65                  70                  75                  80

Arg Thr Phe His Val Leu Leu Ala Arg Leu Leu Glu Asp Gln Gln Val
                 85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Ile Val Arg Ser Ile Ala Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200

<210> SEQ ID NO 3
<211> LENGTH: 35
<212> TYPE: DNA
<213> ORGANISM: Artificial Sequence
```

-continued

```
<220> FEATURE:
<223> OTHER INFORMATION: synthetic

<400> SEQUENCE: 3
gatcgtcgac atggctttca cagagcattc accgc                                    35

<210> SEQ ID NO 4
<211> LENGTH: 39
<212> TYPE: DNA
<213> ORGANISM: Artificial Sequence
<220> FEATURE:
<223> OTHER INFORMATION: synthetic

<400> SEQUENCE: 4
agaaatgaaa cgaaggtcag cgatggacct tactgtcca                                39

<210> SEQ ID NO 5
<211> LENGTH: 39
<212> TYPE: DNA
<213> ORGANISM: Artificial Sequence
<220> FEATURE:
<223> OTHER INFORMATION: synthetic

<400> SEQUENCE: 5
tggacagtaa ggtccatcgc tgaccttcgt ttcatttct                                39

<210> SEQ ID NO 6
<211> LENGTH: 26
<212> TYPE: DNA
<213> ORGANISM: Artificial Sequence
<220> FEATURE:
<223> OTHER INFORMATION: synthetic

<400> SEQUENCE: 6
gaaaccatcg atagcagcac cgtaat                                              26

<210> SEQ ID NO 7
<211> LENGTH: 30
<212> TYPE: DNA
<213> ORGANISM: Artificial Sequence
<220> FEATURE:
<223> OTHER INFORMATION: synthetic

<400> SEQUENCE: 7
gtcaccatgg ctttcacaga gcattcaccg                                          30

<210> SEQ ID NO 8
<211> LENGTH: 42
<212> TYPE: DNA
<213> ORGANISM: Artificial Sequence
<220> FEATURE:
<223> OTHER INFORMATION: synthetic

<400> SEQUENCE: 8
tgacgcggcc gccctacaca ttttcttgtt gttagcaata ta                            42
```

VARIANT OF CILIARY NEUROTROPHIC FACTOR AND DNA ENCODING THE VARIANT

CROSS REFERENCE TO RELATED APPLICATION

The present application is the national stage under 35 U.S.C. 371 of PCT/IT98/00064, filed Mar. 20, 1998.

BACKGROUND OF THE INVENTION

The present invention relates to CNTF variants with enhanced neuronal receptor selectivity, useful for the treatment of neurological or other diseases or disorders.

Ciliary neurotrophic factor (CNTF) is a 23-kDa neurocytokine, which is expressed in both the peripheral and central nervous system beginning in the late embryonic period (reviewed by Manthorpe et al., 1993; Ip and Yancopoulos 1996). Initially identified by its ability to promote the in vitro survival of embryonic chick parasympathetic neurons, CNTF was subsequently shown to exert potent growth-promoting and/or differentiating actions on a variety of neuronal and glial cells, including motoneurons, sensory neurons, sympathetic neurons, hippocampal neurons, and oligodendrocytes (reviewed by Manthorpe et al., 1993; Ip and Yancopoulos 1996). In vivo administration of CNTF prevents degeneration of chick spinal motoneurons during development of axotomized rat facial motoneurons and of motoneurons in mutant progressive motor, neuronopathy mice. The neuroprotective effects of CNTF make it a candidate for the treatment of human motoneuron disease and possibly other neurodegenerative diseases (Manthorpe et al., 1993; Ip and Yancopoulos 1996).

In addition to its neuronal actions, CNTF can also elicit biological effects in non-neuronal cells, such as glia (Hughes et al. 1988; Louis et al. 1993), hepatocytes (Schooltnik et al. 1992), skeletal muscle cells (Helgren et al. 1994), embryonic stem cells (Conover et al.1993), bone marrow stromal cells (Gimble et al.1994), and tumor plasma cells (Zhang et al.1994).

The functional pleiotropy of CNTF is one of the likely reasons for the problems associated with the therapeutic use of this protein. CNTF has a short half-life in vivo (Davies et al., 1994), and needs to be administered at high doses in order to achieve pharmacologically useful concentrations in target tissues. At high dosages CNTF produces side-effects, such as weight loss and acute-phase response (Dittrich et al., 1995). There is therefore a need for agents that are able to mimic the neurotrophic effects of CNTF without eliciting all or part of its side effects.

CNTF exerts its biological actions through the binding, sequential assembly, and activation of a multisubunit receptor complex composed of a ligand-specific a-receptor (CNTFR) and the signal transducing subunits gp130 and leukemia inhibitory factor receptor-b (LIFR) (Ip and Yancopoulos, 1996). Binding of CNTF to CNTFR triggers the subsequent association and heterodimerization of gp130 and LIFR, leading to the activation of a signaling cascade mediated by protein tyrosine kinases of the Jak family and STAT transcription activators. Similar to gp80, the a-receptor for IL-6, which mediates homodimerization of gp130, CNTFR can function in either membrane-bound or soluble forms (Ip and Yancopoulos, 1996). The membrane-bound form of CNTFR (m-CNTFR), which is anchored to the cell surface via a glycosyl-phosphatidylinositol linkage, is expressed predominantly in neuronal and skeletal muscle cells (Davies et al., 1991; Ip et al., 1993). The soluble form of CNTFR (s-CNTFR), which can be produced by phospholipase C-mediated cleavage of m-CNTFR, serves as a cofactor in potentiating CNTF actions on cells that express gp130 and LIFR (Davis et al., 1993). Soluble CNTFR has been detected in cerebrospinal fluid and serum (Helgren et al., 1994; Davis et al., 1993), suggesting that it may be involved in mediating some of the non-neuronal actions of CNTF, such as acute-phase response (Dittrich et al., 1994).

Since m-CNTFR is required for neuronal action of CNTF, while s-CNTFR is thought to mediate non-neuronal effects, modified CNTF proteins with increased selectivity for m-CNTFR are expected to produce a more neuron-specific spectrum of pharmacological activities.

DESCRIPTION OF THE INVENTION

The present invention relates to CNTF variants that, as an effect of specific amino acid substitutions in accordance with the invention, have a reduced ability of binding CNTFR, as compared to the natural CNTF, and a decrease of the biological activity mediated through soluble CNTFR, with an unchanged biological activity mediated through membrane-bound CNTFR.

These variants are on the basis of a method for the treatment of neuronal diseases and disorders, in human and animals. In one embodiment, the biological activities of CNTF variants is compared between human hepatoma cells plus soluble CNTFR and human hepatoma cells stably expressing CNTFR, which provides a method for assessing selectivity for membrane-bound receptor.

In a preferred embodiment, the variant according to the invention is obtained by replacing in the hCNTF (SEQ ID NO: 1) the amino acid threonine in position 169 with isoleucine, and the amino acid histidine in position 174 with alanine (variant which hereinafter is referred as Thr169Ile/His174Ala/hCNTF; IA-CNTF, or SEQ ID NO: 2). This variant is characterized by a reduced ability to bind soluble CNTFR.

The ability of the modified hCNTF to stimulate production of the acute-phase protein haptoglobin is measured in human hepatoma cells in presence of soluble CNTFR. As described hereinafter, the modified CNTF exibits decreased potency as compared to the wild-type CNTF.

In another embodiment, the ability of the modified human CNTF protein to stimulate production of choline acetyltransferase in a human neuroblastoma cell line is measured. As described hereinafter, the modified CNTF protein is equipotent with the wild-type CNTF protein in this assay.

In a preferred embodiment, human hepatoma cells, which do not express CNTFR are engineered to express the full-length human CNTFR, and these cells are used to assay the ability of modified CNTF proteins to stimulate haptoglobin production. Biological activity in this assay is compared to that obtained in parent hepatoma cells assayed in the presence of soluble CNTFR. This procedure provides a measure of selective activation of biological responses through membrane-bound versus soluble CNTFR. As described herein, the modified CNTF protein is equipotent with wild-type human CNTF in this-assay, showing that it maintains high biological activity through membrane-bound CNTFR, while displaying specifically reduced activity through soluble CNTFR. As also described herein, a CNTF variant that was previously shown (Italian patent patent application RM96A000492) to have increased neuronal receptor selectivity (Phe152Ala/Ser166Asp/Gln167His/human CNTF or AKDH-CNTF; a human CNTF variant containing, from amino acids 152 to 167, the sequence reported as SEQ ID NO:3 in the Italian patent application RM96A000492), is also equipotent with wild-type CNTF in hepatoma cells expressing CNTFR. These results shows that this assay system can be used to identify CNTF variants that display different biological activities through soluble and membrane-bound CNTFR.

The ligand retention hypothesis (Baumann et al. 1994) provides the most plausible explanation for the pharmacological behavior of cytokine variants with membrane-bound and soluble receptor isoforms. Baumann and coworkers (see Baumann et al., 1994) calculated that concentrations of cytokine receptors at the cell surface are in the micromolar range (which is far in excess of cytokine-receptor equilibrium dissociation constants, and proposed that this can lead to near unidirectional ligand capture. High membrane concentrations of cytokine receptors would explain why cytokine variants with altered receptor binding affinity can display unchanged agonistic potencies through membrane-bound receptors. The equipotency of CNTF and variants with altered CNTFR affinity in neuronal cells would thus be due to quasi-irreversible ligand capture by in-CNTFR, analogous to the situation in non-neuronal cells in the presence of saturating concentrations of s-CNTFR (Italian patent application RM96A000492).

Thus, according to the invention, certain amino acid substitutions in the human CNTF wild type protein result in modified human CNTF protein that exhibit increased selectivity for membrane-bound (neuronal) vs. soluble (non-neuronal) CNTFR and therefore, would be expected to have enhanced therapeutic properties.

The CNTF modified molecules, useful for practising the present invention, can be prepared by cloning and expressing them in procariotic and eucariotic systems. The resulting recombinant gene can be expressed and purified with any method, allowing the further formation of a stable biologically active protein.

The subject of the present invention is the following.

Variants of the ciliary neurotrophic factor (CNTF) and of the human CNTF wherein the residue of threonine in position 169 is replaced with the residue of isoleucine and the residue of histidine in position 174 is replaced with the residue of alanine. These variants exhibit enhanced selectivity for the (membrane) receptor. Pharmaceutical compositions, comprising the variants of CNTF as per claim 1 or 2 and a pharmaceutically acceptable carrier.

According to the present invention the modified CNTF molecules produced as herein described, or their hybrids or mutants, can be used for promoting the differentiation, proliferation or surviving in vitro or in vivo of cells responding to CNTF. The present invention can be used for treating pathologies of any cell responding to CNTF, in the preferred embodiments, pathologies of neuronal cells expressing membrane-bound CNTF receptor, can be treated.

Method for assessing the enhanced selectivity for membrane-bound receptor of the variants of CNTF is inducing biological responses through membrane-bound CNTF receptor or soluble CNTF receptor Variants of. CNTF, selected by the above method. Isolated and purified DNA molecules which code for the CNTF variants. DNA recombinant molecules which comprise the above DNA functionally bound to a sequence for controlling the expression in said recombinant DNA. Unicellular host transformed with the recombinant DNA, the unicellular host can be selected from the group comprising bacteria, yeasts, fungi and animal and vegetal cells. Use of the above variants for the preparation of drugs for the treatment of neurological diseases or disorders.

These neurological diseases or disorders include degenerative pathologies as retinal pathologies, diseases or pathologies involving spinal cord, colinergic neurones, hyppocampus neurones, or diseases or pathologies involving motorial neurones.

The variants according to the present invention can be used also in the treatment of diseases or pathologies deriving from nervous system damages, caused by traumas, surgery operations, heart attack, infections and malignant tumours, or by the exposition to tossic agents. Coniugates of the above variants with other proteins or other molecules. Coniugates of the above variants with antibodies against the transferring receptor for allowing the variants to cross the blood-brain barrier. Coniugates of the above variants with polyehtylenglicol for reducing the immunogenicity of said variants.

FIG. 1 shows CNTFR binding of CNTF and IA-CNTF. Binding of biotinylated human CNTF to immobilized CNTFR was determined in the absence (control) or presence of CNTF (•), or IA-CNTF (○). Results are expressed as percent to control binding and represent the mean ±deviation from duplicate determinations. Data are from a representative experiment that was repeated three times with similar results.

Figure 2:
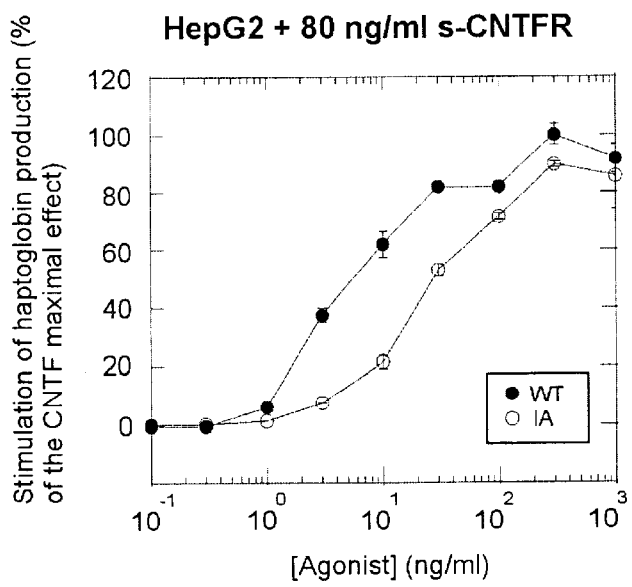

FIG. 2 shows s-CNTFR-medicated biological activity in HepG2 cells. Stimulation of haptoglobin production in HepG2 cells was determined in the presence of 80 ng/ml s-CNTFR, and CNTF (•)of IA-CNTF (○). Results are expressed as a percentage of the maximal CNTF-induced response. Each point is the mean=s.e.m. form at least two separate experiments.

Figure 3:
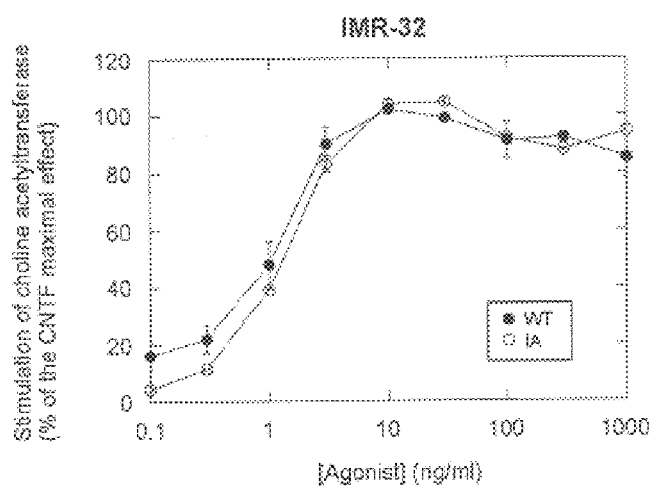

FIG. 3 shows m-CNTFR-medicated biological activity in IMR-32 cells. Induction of choline acetyltransferase (Chat) activity in IMR-32 cells by CNTF (•) or IA-CNTF (○) was determined. Results are expressed as a percentage of the maximal CNTF-induced response. Each point is the near ±s.e.m. from duplicate culture dishes.

Figure 4:
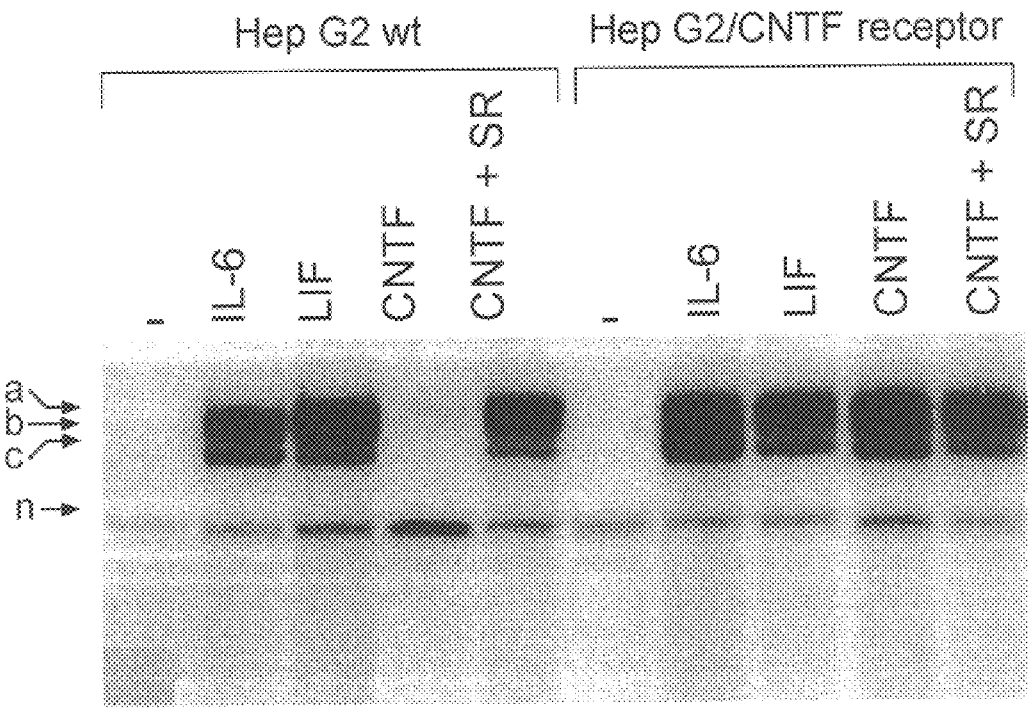

FIG. 4 shows early signaling responses medicated by the combination of CNTF+s-CNTFR in HepG2 cells and CNTF in HepG2/CNTFR cells. Cells were either not treated with any cytokine (-) or treated for 15 min with 100 ng/ml IL-6, LIF, CNTF, of 100 ng/ml s-CNTFR plus 100 ng/ml CNTF (CNTF+s-R). Activation of cellular STAT factors was determined by electromobility shift assay. Arrows denote the positions of migration of bound STAT3 homodimers (a), Stat1:Stat3 heterodimers (b), Stat1 homodimers (c), in the figure n indicates a non-specific binding.

Figure 5:
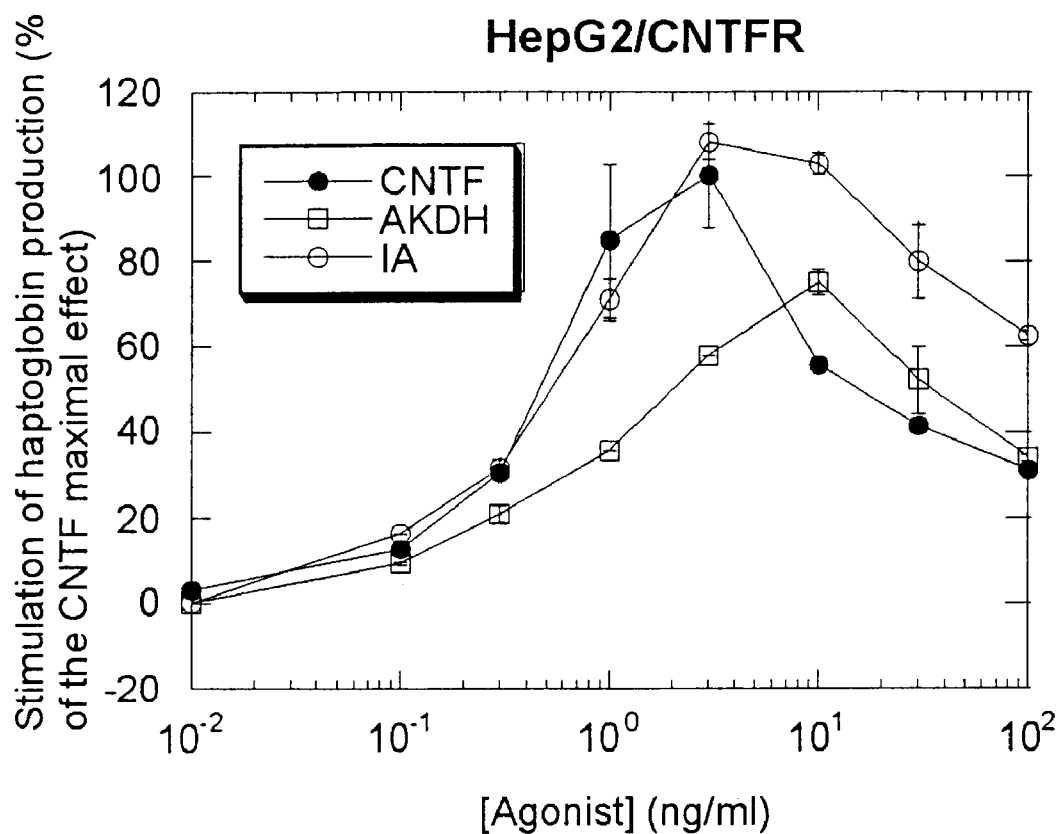

FIG. 5 shows m-CNTFR-medicated biological activity in HepG2/CNTFR cells. Experimental details and treatment of results were as described in the FIG. 2 legend. The proteins tested were CNTF (•), IA-CNTF (○), and AKDH-CNTF (□).

Deposits

*E. Coli* HB2151 bacteria, transformed with a nucleotide sequence coding for SEQ ID NO:2 was filed on Feb. 12, 1997 with The National Collections of Industrial and Marine Bacteria Ltd. (NCIMB), Aberdeen, Scotland, UK. under access numbers NCIMB 40860.

Up to this point a general description has been given of the present invention. With the aid of the following examples, a more detailed description of specific embodiments thereof will now be given, in order to give a clearer understanding of its objects, characteristics, advantages and method of operation.

EXAMPLES

Example 1

Preparation of Modified CNTF Protein a) Construction of DNA Coding for Modified CNTF Protein Thr169Ile/His174Ala/human CNTF (IA-CNTF; SEQ ID NO:2):, was prepared. Mutations were generated by overlap extension PCR (Horton and Pease, 1991), using the pHenD-CNTF vector (Baumann et al. 1993) as template. Two separate PCR amplifications were performed using the oligonucleotide primer sets 1 (5'-GATCGTCGACATGGCTTTCACAGAGCATTCACCGC-3') (SEQ ID NO:3)+2 (5'-AGAAATGAAACGAAGGTCAGCGATGGACCTTACT GTCCA-3') (SEQ ID NO:4) and 3 (5'-TGGACAGTAAGGTCCATCGCTGACCTTCGTTTCAT TTCT-3') (SEQ ID NO:5)+4 (5'-GAAACCATCGATAGCAGCACCGTAAT-3')(SEQ ID NO:6), with cycles of 2 min at 94o, 2 min at 50°, and 3 min at 72°. The two PCR products were isolated using a Qiaex kit, mixed, and amplified in a second PCR reaction. Five PCR cycles (as above) were performed in the absence, and 35 cycles in the presence of primers 1+4. The PCR product was digested with SalI and ClaI, purified by Qiaex, and subcloned into the SalI/ClaI-digested pHenD-CNTF vector, yielding the vector pHenD-IA-CNTF. DNA sequencing revealed the presence of a mutation producing the His174Ala substitution expected from the mutagenized primers used, as well as an additional point mutation (probably due to an error of the polymerase) which gives rise to a Thr169Ile substitution in the encoded protein sequence. The coding sequence for IA-CNTF was subcloned into the pRSET plasmid, which allows high-level protein expression in bacteria (Horton and Pease, 1991), using the following procedure. PCR amplification was performed with the pHenD-IA-CNTF vector as template, using the oligonucleotide primers 5 (5'-GTCACCATGGCTTTCACAGAGCATTCACCG-3') (SEQ ID NO:7) and 6 (5'-TGACGCGGCCGCCCTACACATTTTCTTGTTGTTAGC AATATA-3')(SEQ ID NO:8), with 25 cycles of 2 min at 94°, 2 min at 50°, and 2 min at 72°. The PCR product was digested with NcoI and BamHI, purified using a Wizard PCR kit, and subcloned into the NcoI/BamHI-digested plasmid pRSET-CNTF (Horton and Pease, 1991). The identity of the final construct was confirmed by DNA sequencing.

b) Production and Purification of Modified CNTF Protein

Recombinant proteins were produced in *E. coli* and purified by reverse-phase HPLC according to previously described procedures (Saggio et al., 1995; Di Marco et al., 1996).

Example 2

Receptor Binding Activity of Modified CNTF Protein

The CNTFR binding activity of CNTF and IA-CNTF was determined by measuring the ability of the proteins to compete with biotinylated CNTF for binding to solid phase-immobilized CNTFR, using a previously described procedure (Saggio et al., 1994; Saggio et al., 1995). As shown in FIG. 1, IA-CNTF displayed 15-fold reduced affinity for CNTFR, as compared to the wild-type protein.

Example 3

Biological Activity Mediated Through Soluble CNTFR in Non-neuronal Cells

Stimulation of Haptoglobin Production in HepG2 Cells

The human hepatoma cell line HepG2 expresses LIFR and gp130, but not CNTFR (Baumann et al., 1993). Addition of soluble CNTFR to HepG2 cells causes a dose-dependent increase in responsiveness to CNTF, due to formation of high affinity CNTF receptor complexes. The biological activity of IA-CNTF is depicted in FIG. 2. At a subsaturating concentration of s-CNTFR, this variant behaved as a full agonist in the HepG2 assay, with an EC50 value 5 times higher than that of CNTF, in agreement with its reduced affinity; for CNTFR.

Example 4

Biological Activity Mediated Through Membrane-Bound CNTFR in Neuronal Cells Stimulation of Choline Acetyltransferase Activity in IMR-32 Cells The ability of CNTF and IA-CNTF to induce choline acetyltransferase in the human neuroblastoma cell line IMR-32, which expresses m-CNTFR (Baumann et al.,1993; Halvorsen et al., 1996) was determined. In contrast to HepG2 cells, CNTF and IA-CNTF were equipotent in this assay, as it is evidenced in the FIG. 3.

Example 5

Biological Activity in Non-neuronal Cells Engineered to Express Membrane-Bound CNTFR To test whether membrane-bound CNTFR was sufficient to confer high responsiveness to a modified CNTF protein despite its reduced affinity for CNTFR, HepG2 cells were stably transfected with an expression vector encoding full-length CNTFR. To this end, human cDNA encoding the full-length human CNTFR (nucleotides 264–1382 coding for amino acids 1-372 (Davis et al., 1991).) was obtained by reverse transcription-PCR from SH-SY5Y cells and cloned into the EcoRV site of the eukaryotic expression plasmid pcDNA3 (Invitrogen), which carries the neomycin resistance gene. DNA (20 mg) was transfected into HepG2 cells as a calcium phosphate precipitate (Graham and Van der Eb, 1973), and cells were subjected to selection in complete culture medium (minimal essential medium containing penicillin, streptomycin, and lot fetal calf serum) supplemented with 1 mg/ml G418. A subclone stably expressing CNTFR (HepG2/CNTFR) was identified on the basis of CNTF surface binding and CNTF-induced stimulation of haptoglobin production. HepG2/CNTFR cells were maintained in complete culture medium supplemented with 0.2 mg/ml G418.

The presence of functional m-CNTFR in HepG2/CNTFR cells was confirmed by the ability of CNTF to rapidly induce the activation of STAT transcription factors in the absence of s-CNTFR. In contrast, STAT activation by CNTF in HepG2 cells required the presence of s-CNTFR, as shown in FIG. 4.

Electromobility Shift Assay

HEPG2 and HEPG2/CNTFR cells were plated in 100 ml Petri dishes, and used 24 h later, when they are semi-confluent. Cells were serum starved for 4 h, before be treated for 15 minutes with various reagents. Cells were then washed with an ice solution of phoshate salt buffer, containing NaF 50 mM, collected through centrifugation and frozen in liquid N2. Total cell extracts were prepared as previously described (Demartis et al., 1996). The high affinity binding of the activated STAT factors with the oligonucleotide SIE m67 (Wagner et al., 1990) was determined with electromobility shift assay according to Sadowsky and Gilman (see Sadowsky and Gilman, 1993) using 10 (g of cell extract. The oligonucleotide probe was labeled in the 5' end, with Klenow enzyme in presence of [(-32P] dATP and [(-32P]dCTP (3000 Ci/mmoli). Complexes were solved in polyacrilammide gel 5% glycerol in 2,5%/0,5 TBE (Tris-borato 45 mM, EDTA 0,5 mM, pH 7,8), then dryed and subjected to autoradiography.

CNTF and IA-CNTF were equipotent in stimulating haptoglobin production in HeG2/CNTFR cells (FIG. 5), showing that membrane anchoring of CNTFR in non-neuronal cells is sufficient to confer a profile of relative biological activities similar to that observed in neuronal IMR-32 cells. AKDH-CNTF (Phe152Ala/Ser166Asp/Gln167His/human CNTF), a human CNTF variant that was previously shown (Italian patent patent application RM96A000492) to have increased neuronal receptor selectivity, is also very potent in hepatoma cells expressing CNTFR. These results show that this assay can serve to identify CNTF variants with increased selectivity for membrane-bound CNTFR.

REFERENCES (1) Manthorpe, M., Louis, J. C., Hagg, T., e Varon, S. (1993) in Neurotrophic factors (Loughlin, S. E. e Fallon, J. H., eds) p. 443–473, Academic Press, San Diego,. Calif.
(2) Ip, N. Y. e Yancopoulos, G. D. (1996) Annu. Rev. Neurosci. 19, 491–515
(3) Hughes, S. M. Lillien, L. E., Raff, M. C., Rohrer, H.,e Sendtner, M. (1988) Nature 335, 70–73
(4) Louis, J. -C., Magal, E., Takayama, S., e Varon, S. (1993) Science 259, 689–692
(5) Schooltink, H., Stoyan, T., Roeb, E., Heinrich, P. C., e Rose-John, S. (1992) FEBS Lett. 314, 280–284
(6) Helgren, M. E., Squinto, S. P., Davis, H. L., Parry, D. J., Boulton, T. G., Heck, C. S., Zhu, Y., Yancopoulos, G. D., Lindsay, R. M., e DiStefano, P. S. (1994) Cell 76, 493–504
(7) Conover, J. C., Ip, N. Y., Poueymirou, W. T., Bates, B., Goldfarb, M. P., DeChiara, T. M., e Yancopoulos, G. D. (1993) Development 119, 559–565
(8) Gimble, J. M., Wanker, F., Wang, C. -S., Bass, H., Wu, X., Kelly, K., Yancopoulos, G. D., e Hill, M. R. (1994) J. Cell. Biochem. 54, 122–133
(9) Zhang, X. -G., Gu, J. -J., Lu, Z. -Y., Yasukawa, K., Yancopoulos, G. D., Turner, K., Shoyab, M., Taga, T., Kishimoto, T., Bataille, R., e Klein, B. (1994) J. Exp. Med. 177, 1337–1342
(10) Dittrich, F., Thoenen, H., e Sendtner, M. (1994) Ann. Neurol. 35, 151–163
(11) Davis, S., Aldrich, T. H., Valenzuela, D. M., Wong, V., Furth, M. E., Squinto, S. P., e Yancopoulos, G. D. (1991) Science .253, 59–63
(12) Ip, N. Y., McClain, J., Barrezueta, N. X., Aldrich, T. H., Pan, L., Li, Y., Wiegand, S. J., Friedman, B., Davis, S., e -Yancopoulos, G. D. (1993) Neuron 10, 89–102
(13) Davis, S., Aldrich, T. H., Ip, N.Y., Stahl, N., Scherer, S., Farruggella, T., DiStefano, P. S., Curtis, R., Panayotatos, N., gascan, H., Chevalier, S., e Yancopoulos, G. D. (1993) Science 259, 1736–1739.
(14) Baumann, G., Lowman, H. B., Mercado, M., e Wells, J. A. (1994) J. Clin. Endocrinol. Metab. 78, 1113–1118
(15) Horton, R. M. e Pease, L. R. (1991) in Directed mutagenesis: a practical approach, (ed. McPherson, M. J.) Oxford Univ. Press, Oxford, pp. 217–247
(16) Saggio, I., Paonessa, G., Gloaguen, I., Graziani, R., Di Setio, A., e Laufer, R. (1994) Anal. Biochem. 221, 387–391
(17) Saggio, I., Gloaguen, I., Poiana, G., e Laufer, R. (1995) EMBO J. 14, 3045–3054
(18) Di Marco, A., Gloaguen, I., Graziani, R., Paonessa, G., Saggio, I., Hudson, K. R., e Laufer, R. (1996) Proc. Natl. Acad. Sci. USA 93, 9247–9252
(19) Baumann, H., Ziegler, S. F., Mosley, B., Morella, K. K., Pajovic, S., e Gearing, D. P. (1993) J. Biol. Chem. 268, 8414–8417
(20) Halvorsen, S. W., Malek, R., Wang, X., e Jiang, N. (1996) Neuropharmacology 35, 257–265
(21) Graham, F. L. and Van der Eb, A. J. (1973) Virology 52, 456–461
(22) Demartis, A., Bernassola, F., Savino, R., Melino, G., e Ciliberto, G. (1996) Cancer Res. 56, 4213–4218
(23) Wagner, B. J., Hayes, T. E., Hoban, C. J., e Cochran, B. H. (1990) EMBO J. 9, 4477–4484
(24) Sadowski, H. B. e Gilman, M. Z. (1993) Nature 362, 79–83
(25) Gearing, D. P. (1993) Adv. Immunol. 53, 31–58

What is claimed is:

1. A variant of the ciliary neurotrophic factor (CNTF), characterized in that the residues in the positions corresponding to the positions 169 and 174 of the human CNTF wild type (SEQ ID NO:1) are replaced with the residue of isoleucine and the residue of alanine respectively, said variant exibiting an unaltered binding affinity for the CNTF membrane receptor with respect to the CNTF wild type and a reduced binding affinity for the soluble CNTF receptor with respect to the CNTF wild type.

2. The variant of the CNTF according to claim 1, wherein said CNTF, said CNTF membrane receptor and said CNTF soluble receptor are human.

3. A DNA molecule coding for the CNTF variant according to claim 1.

4. The DNA molecule according to claim 3, wherein said DNA molecule is an isolated and purified DNA molecule.

5. A DNA recombinant molecule which comprises the DNA molecule according to claim 4 operatively linked to a sequence controlling the expression of said DNA molecule in said recombinant DNA molecule.

6. A host cell transformed with the recombinant DNA molecule according to claim 5.

7. The host cell according to claim 6, wherein said host cell is selected from the group consisting of bacteria, yeasts, fungi, animal cells and plant cells.

8. A method for stimulating in vitro production of choline acetyltransferase in a human neuroblastoma cell comprising the step of providing externally to said cell in vitro the variant of CNTF of claim 1 such that production of choline acetyltransferase is stimulated.

9. The variant of CNTF according to claim 1, wherein said variant is isolated.

10. The variant of CNTF according to claim 2, wherein said variant is isolated.

* * * * *